US011806719B2

United States Patent
Beer et al.

(10) Patent No.: US 11,806,719 B2
(45) Date of Patent: Nov. 7, 2023

(54) INTEGRATED SOLID-STATE RAPID THERMO-CYCLING SYSTEM

(71) Applicant: Lawrence Livermore National Security, LLC, Livermore, CA (US)

(72) Inventors: N. Reginald Beer, Pleasanton, CA (US); Gary Johnson, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 17/816,886

(22) Filed: Aug. 2, 2022

(65) Prior Publication Data
US 2023/0166265 A1 Jun. 1, 2023

Related U.S. Application Data

(62) Division of application No. 16/058,953, filed on Aug. 8, 2018, now Pat. No. 11,440,015.

(51) Int. Cl.
*B01L 7/00* (2006.01)
*B01L 99/00* (2010.01)
(Continued)

(52) U.S. Cl.
CPC ............ *B01L 7/525* (2013.01); *C12Q 1/6869* (2013.01); *H10N 10/13* (2023.02); *B01L 2300/1805* (2013.01)

(58) Field of Classification Search
CPC ..... B01L 2300/0829; B01L 2300/1805; B01L 2300/1822; B01L 2300/1844; B01L 7/52; B01L 7/525; C12Q 1/6869; H10N 10/13
See application file for complete search history.

(56) References Cited

U.S. PATENT DOCUMENTS 5,641,400 A 6/1997 Kaltenbach et al.
5,834,252 A 11/1998 Stemmer et al.
(Continued)

FOREIGN PATENT DOCUMENTS

WO 2008070198 A2 6/2008
WO 2009094061 A1 7/2009
(Continued)

OTHER PUBLICATIONS

Beer, N.R. et al., "On-Chip Single-Copy Real-Time Reverse-Transcription PCR in Isolated Picoliter Droplets," Anal. Chem., 2008, pp. 1854-1858, vol. 80, No. 6.
(Continued)

*Primary Examiner* — Lydia Edwards
(74) *Attorney, Agent, or Firm* — Perkins Coie LLP

(57) ABSTRACT

Techniques, systems, and devices are disclosed for implementing a portable lab system for PCR testing. An example method for operating an integrated thermal cycling system includes depositing samples into the integrated thermal cycling system that includes a thermal cycling device and an electronic interface. The thermal cycling device includes multiple wells to receive the samples to be thermally cycled, a thermoelectric cooling (TEC) element connected to the multiple wells, a substrate on which the TEC element is positioned, and a controller coupled to the TEC element. The multiple wells are positioned within the substrate that includes a thermally conductive ground positioned between adjacent wells. Supplying power to the integrated thermal cycling system, via the electronic interface, allows the multiple wells to exchange heat with the substrate and for each well to operate independently from other wells.

16 Claims, 9 Drawing Sheets

(51) Int. Cl.
*C12Q 1/6869* (2018.01)
*H10N 10/13* (2023.01)

(56) References Cited

U.S. PATENT DOCUMENTS

| | | | |
|---|---|---|---|
| 5,882,465 | A | 3/1999 | Mcreynolds |
| 7,578,976 | B1 | 8/2009 | Northrup et al. |
| 7,585,663 | B2 | 9/2009 | Shigeura et al. |
| 7,665,311 | B2 | 2/2010 | Steffensen et al. |
| 8,720,209 | B1 | 5/2014 | Beer et al. |
| 2002/0119535 | A1 | 8/2002 | Slater et al. |
| 2003/0165946 | A1 | 9/2003 | Evans |
| 2005/0282224 | A1 | 12/2005 | Fouillet et al. |
| 2006/0042785 | A1 | 3/2006 | Werner et al. |
| 2006/0094108 | A1 | 5/2006 | Yoder et al. |
| 2008/0022647 | A1 | 1/2008 | Jones |
| 2008/0166793 | A1 | 7/2008 | Beer et al. |
| 2008/0270030 | A1 | 10/2008 | Copley |
| 2009/0226971 | A1 | 9/2009 | Beer et al. |
| 2009/0226972 | A1 | 9/2009 | Beer et al. |
| 2010/0091459 | A1 | 4/2010 | Zhang |
| 2010/0101237 | A1 | 4/2010 | Wu et al. |
| 2010/0233763 | A1 | 9/2010 | Shigeura et al. |
| 2017/0021356 | A1 | 1/2017 | Dority et al. |

FOREIGN PATENT DOCUMENTS

| | | |
|---|---|---|
| WO | 2010093249 A2 | 8/2010 |
| WO | 2011028924 A2 | 3/2011 |

OTHER PUBLICATIONS

Beer, N.R. et al., "On-chip, real-time, single-copy polymerase chain reaction in picoliter droplets," Anal. Chem., 2007, pp. 8471-8475, vol. 79.

Finnzymes, Inc., "24-well and 96-well Piko Thermal Cyclers," Jun. 20, 2010, four pages. [Online] [Retrieved Jan. 24, 2012] Retrieved from the Internet <URL:http://web.archive.org/web/20100620081305/http://www.finnzymes.us/Piko/thermalcyclers.html.>.

Fujimoto, T. et al., "Novel High-Speed Real-Time PCR Method (Hyper-PCR): Results from Its Application to Adenovirus Diagnosis," Jpn. J. Infect. Dis., 2010, pp. 31-35, vol. 63.

Griep, M.A. et al., "Kinetics of the DNA Polymerase Pyrococcus kodakarensis," Chemical Engineering Science, 2006, pp. 3885-3892, vol. 61.

Khanafer, K. et al., "Isothermal Surface Production and Regulation for High Heat Flux Applications Utilizing Porous Inserts," International Journal of Heat and Mass Transfer, 2001, pp. 2933-2947, vol. 44.

Kim, Y.H. et al., "Performance Evaluation of Thermal Cyclers for PCT in a Rapid Cycling Condition," BioTechniques, 2008, pp. 495-505.

Kiss, M. et al., "High-Throughput Quantitative Polymerase Chain Reaction in Picoliter Droplets," Anal. Chem., 2008, pp. 8975-8981, vol. 80, No. 23.

Ksiazek, T. et al.,"A Novel Coronavirus Associated with Severe Acute Respiratory Syndrome," New England Journal of Medicine, 2003, pp. 1953-1966, vol. 348, No. 20.

Lee, W.-G. et al., "Nano/Microfluidics for diagnosis of infectious diseases in developing countries," Advanced Drug Delivery Reviews, 2010, pp. 449-457, vol. 62, No. 4-5.

Mahjoob, S. et al., "Rapid Microfluidic Thermal Cycler for Polymerase Chain Reaction Nucleic Acid Amplification," International Journal of Heat and Mass Transfer, 2008, pp. 2109-2122, vol. 51.

Maltezos, G. et al., "Thermal Management in Microfluidics Using Micro-Peltier Junctions," Applied Physics Letters, 2005, pp. 154105-1 to 154105-3, vol. 87.

Neuzil, P. et al., "Ultra fast miniaturized real-time PCR: 40 cycles in less than six minutes," Nucleic Acids Res., 2006, vol. 34, No.11, nine pages.

Smiths Detection, "Bio-Seeq PLUS: Feature Highlights," 2012, two pages. [Online] [Retrieved Jan. 24, 2012] Retrieved from the Internet <URL:http://www.smithsdetection.com/Bio-Seeq-PLUS.>.

Terazono, H. et al., "Development of a High-Speed Real-Time Polymerase Chain Reaction System Using a Circulating Water-Based Rapid Heat-Exchange," Japanese Journal of Applied Physics, Jun. 2010, pp. 06GM05-1 to 06GM05-5, vol. 49, No. 6, Issue 2 of 2.

Tewhey, R. et al., "Microdroplet-based PCR enrichment for large-scale targeted sequencing," Nature Biotechnology, Nov. 2009, pp. 1025-1031, vol. 27, No. 11.

Wang, Y. et al., "A Novel Strategy to Engineer DNA Polymerases for Enhanced Processivity and Improved Performance in Vitro," Nucleic Acids Res., 2004, pp. 1197-1207, vol. 32, No. 3.

Zhang, C. et al., "Miniaturized PCR chips for nucleic acid amplification and analysis: latest advances and future trends," Nucleic Acids Research, 2007, pp. 4223-4237, vol. 35, No. 13.

USB 3.1 Standard-A Connector Pin Assignments

| Pin Number[1] | Signal Name[2] | Description | Mating Sequence[3] |
|---|---|---|---|
| 1 | VBUS | Power | Third |
| 2 | D- | USB 2.0 differential pair | Fourth |
| 3 | D+ | | |
| 4 | GND | Ground for power return | Third |
| 5 | StdA_SSRX- | SuperSpeed receiver differential pair | Last |
| 6 | StdA_SSRX+ | | |
| 7 | GND_DRAIN | Ground for signal return | |
| 8 | StdA_SSTX- | SuperSpeed transmitter differential pair | |
| 9 | StdA_SSTX+ | | |
| 12[4], 13 | INSERTION DETECT | Receptacle only. Detects insertion of a plug into the receptacle. Optional except for cold socket applications. See the Universal Serial Bus Power Delivery Specification for details. | Second |
| Shell | Shield | Connector metal shell | First |

Note 1: Pin numbers not included in this table do not have contacts present.
Note 2: Tx and Rx are defined from the host perspective.
Note 3: The mating sequence assumes support of INSERTION DETECT.
Note 4: Pin 12, if present, shall be connected to Shield.

FIG. 7

INTEGRATED SOLID-STATE RAPID THERMO-CYCLING SYSTEM

CROSS-REFERENCE TO RELATED APPLICATION(S)

This patent document is a divisional of and claims the benefit of priority to U.S. patent application Ser. No. 16/058,953, filed on Aug. 8, 2018. The entire contents of the before-mentioned patent application are incorporated by reference as part of the disclosure of this application.

STATEMENT REGARDING FEDERALLY SPONSORED RESEARCH OR DEVELOPMENT

This invention was made with Government support under Contract No. DE-AC52-07NA27344 awarded by the United States Department of Energy. The Government has certain rights in the invention.

TECHNICAL FIELD

This patent document relates to systems, devices, and processes that use rapid thermal cycling technologies and, in particular, the integration of a rapid solid-state thermal cycler into a portable lab system.

BACKGROUND

Polymerase chain reaction (PCR) is an indispensable technique in medical and biological research laboratories around the world. It allows researchers and clinicians to produce millions of copies from a single piece of DNA or RNA for use in genome sequencing, gene analysis, inheritable disease diagnosis, paternity testing, forensic identification, and the detection of infectious diseases. By its very nature, the method utilizes an exponential increase in signal, allowing detection of even single-copy nucleic acids in complex, real environments. Accordingly, PCR systems are ubiquitous, and the market for a faster thermo-cycling method is significant.

SUMMARY

Techniques, systems, and devices are disclosed for implementing a portable lab system for PCR testing.

One exemplary aspect of the disclosed technology relates to a portable lab system that includes a thermal cycling device including a first well and a second well to receive samples to be thermally cycled, a thermoelectric cooling (TEC) element coupled to the first well and the second well, and a substrate comprising a thermally conductive ground configured to allow the first well and the second well to exchange heat with the substrate and to operate independently from one another. The portable lab system also includes a controller to control operation of the TEC element, as well as an electronic interface including a power interface to supply power to the TEC element and the controller of the thermal cycling device to allow the TEC element to transfer energy from the first well to the second well when current flows through the TEC element in a first direction, and from the second well to the first well when current flows through the TEC element in a second direction, and a data interface to collect data from the controller.

In another exemplary aspect, a method of operating an integrated thermal cycling system is disclosed. The method comprises depositing samples into the integrated thermal cycling system; coupling the integrated thermal cycling system to a computing device via an electronic interface; supplying power to the integrated thermal cycling system, via the electronic interface, to allow the samples to be thermally cycled; and displaying, via n user interface on the computing device, the data collected by the integrated thermal cycling system.

The above and other aspects and their implementations are described in greater detail in the drawings, the description and the claims.

BRIEF DESCRIPTION OF THE DRAWINGS

FIG. 7 illustrates the pin assignments for a USB 3.1 standard-A connector.

DETAILED DESCRIPTION

Figure 1:
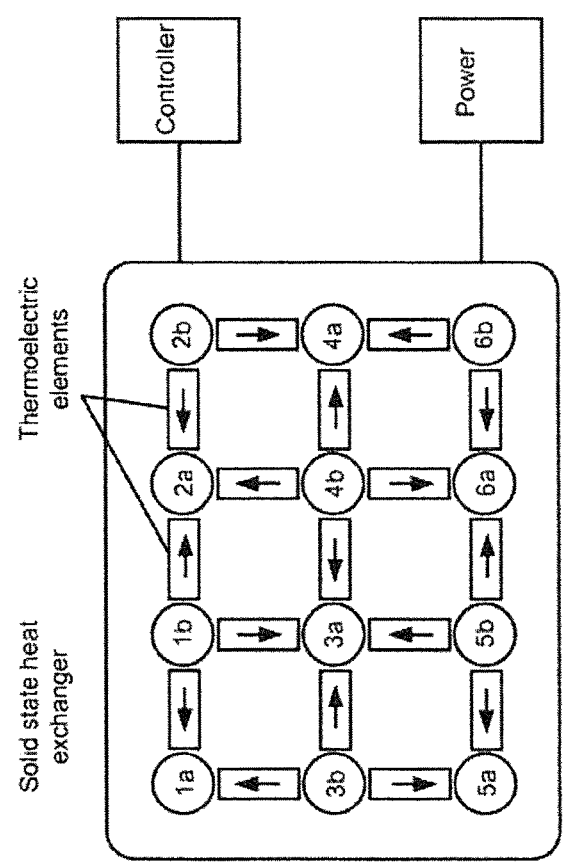
FIG. 1 shows an exemplary configuration of a solid-state rapid thermocycler.

Solid-state thermal cycling provides thermal cycling between wells connected by semiconductor or printed Thermal Electric Coolers (TECs). These linked wells work in tandem to trade thermal energy cyclically to power repeated heating and cooling applications such as PCR. FIG. 1 shows an exemplary configuration of a solid-state rapid thermocycler. In this configuration, a single well or a row of wells exchanges thermal energy with other wells or rows of wells while waste heat exits to the substrate. More configurations of the rapid thermocycler are described in U.S. Pat. No. 8,720,209, filed on Oct. 6, 2011, which is hereby incorporated by reference in its entirety.

One advantageous aspect of the above-mentioned thermocycler is its ability to swap heat between wells, providing efficiency in the thermal load with less wasted heat. However, the wells operate dependently by having the wells in the same range of temperature swing and cycle time, unless the thermocycler is further equipped with resistive heaters.

This patent document describes techniques, systems, and devices to allow, among other features and benefits, each well to be operated independently of each other such that the wells can have separate thermal set points and cycle durations.

Figure 2:
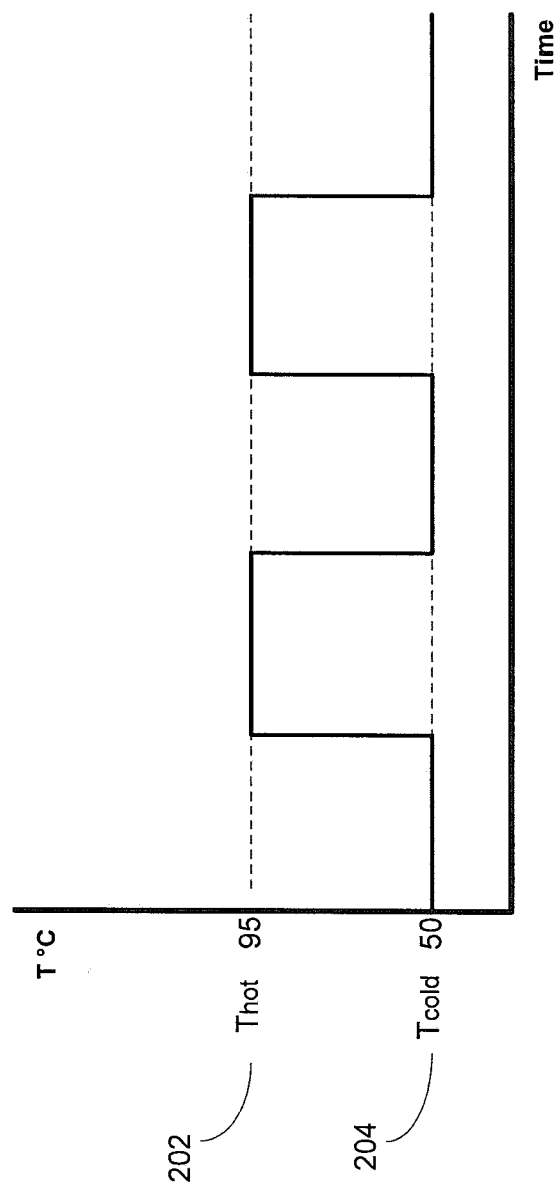
FIG. 2 shows an exemplary plot of well thermal history for PCR.
Figure 3:
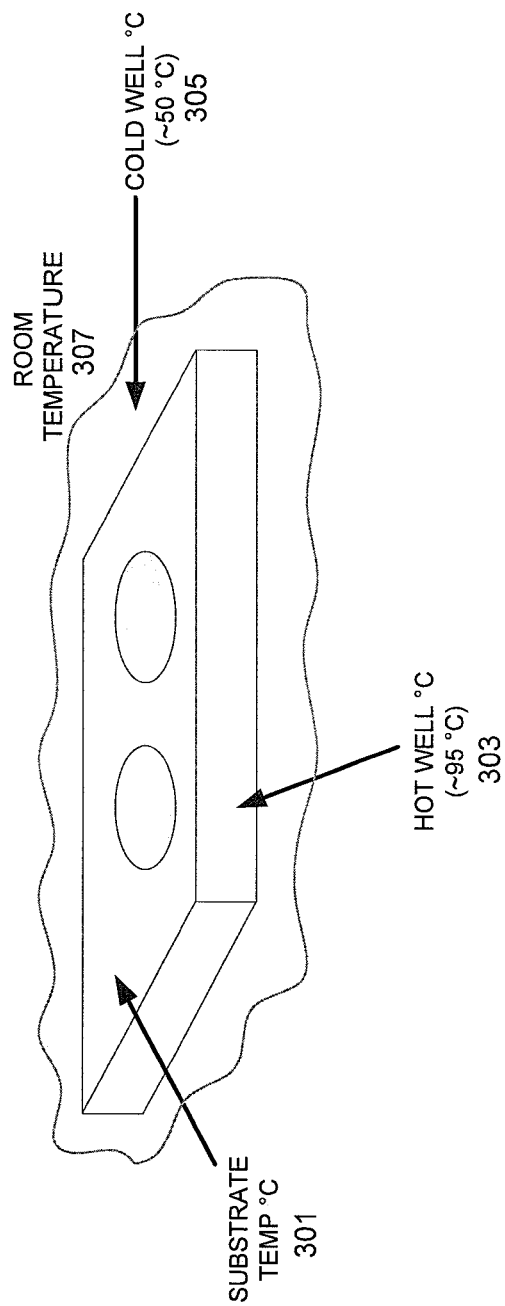
FIG. 3 illustrates different temperatures present around the thermal cycling device when it is in operation.
Figure 4:
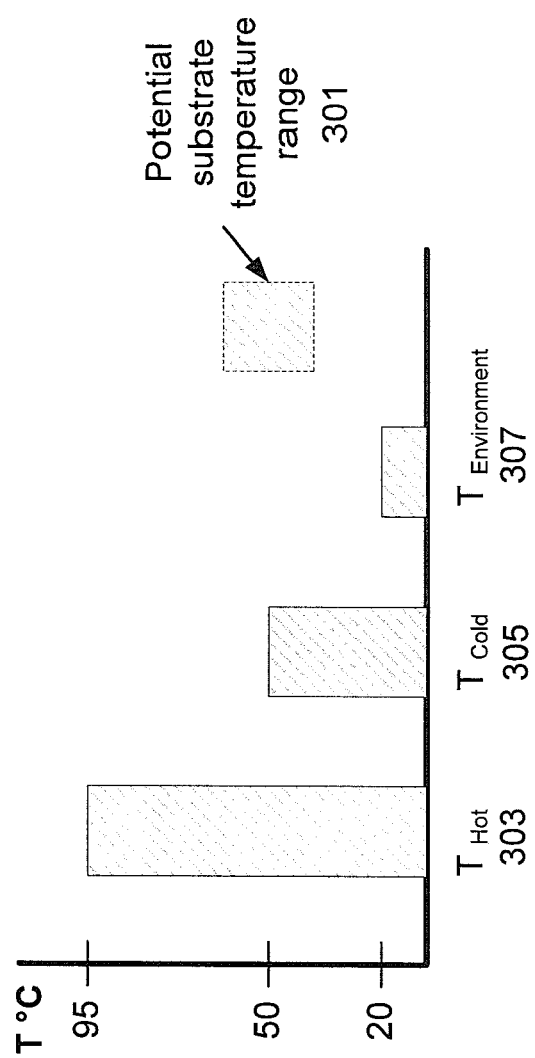
FIG. 4 shows an exemplary plot of potential substrate temperature range.

FIG. 2 shows an exemplary plot of well thermal history for PCR. The temperature for a hot well $T_{hot}$ 202 can be around 95°, while the temperature for a cold well $T_{cold}$ 204 can be around 50°. FIG. 3 illustrates different temperatures around the thermal cycling device when it is in operation. The substrate temperature $T_{substrate}$ 301 is usually lower than $T_{hot}$ 303 due to thermal exchange, such as radiation, convection, and conduction, with the environment at room temperature $T_{room}$ 307. FIG. 4 shows an exemplary plot of potential substrate temperature range. Depending on the substrate design and features, $T_{substrate}$ 301 may be lower, higher, or substantially equivalent to $T_{cold}$ 305.

Figure 5:
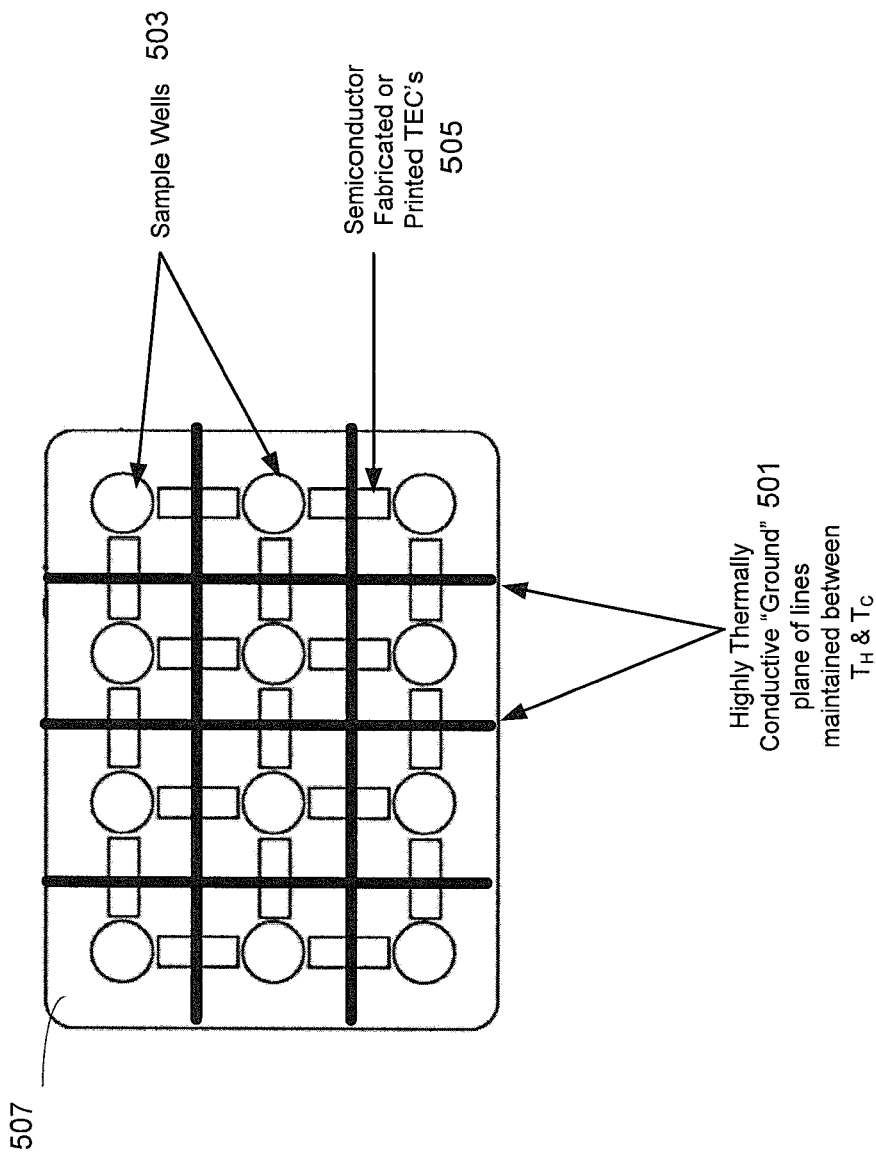
FIG. 5 shows a schematic configuration of an exemplary solid-state rapid thermocycler with an intermediate thermal ground.

FIG. 5 shows a schematic configuration of an exemplary solid-state rapid thermocycler with an intermediate thermal ground 501. Sample wells 503 are connected by semiconductor or printed Thermal Electric Coolers (TECs) 505. The intermediate thermal ground 501 provides an opportunity to break inter-well thermal cycling dependency by allowing wells 503 to individually exchange heat with the substrate 507 instead of each other. The thermal ground 501 can be a thermal ground lattice, line, trace, or plane. It can be constructed out of materials with appropriate thermal conductivity and specific heat capacity to provide optimal heat transfer and buffering. For example, copper, aluminum, and conductive alloys, as well as ceramics and other materials may be used.

The thermal ground 501 can act as a conduction cooling device, transferring heat to an external fan, heat sink, Peltier TEC, radiator fins, or other heat transfer and/or storage device. Furthermore, the sample wells 503 can be independent of each other, insulated from each other, but in excellent thermal and semiconductor TEC 505 contact with the ground plane. The physical geometry of the thermal ground lines or lattice can be an interspaced grid, such as a waffle iron pattern between individual wells, an outline rectilinear shape outside of the wells, or a radial geometry in which the thermal ground line is a concentric ring outside or inside a plurality of sample wells. In some embodiments, the thermal ground plane 501 does not carry electrical current, and is insulated from the individual TEC electrical power lines.

In one advantageous aspect, this configuration as shown in FIG. 5 provides independent well operation that allows different wells to have separate thermal set points and cycle durations. Different samples requiring different thermocycling temperatures, therefore, can be tested in different wells at the same time. In another advantageous aspect, the configuration can also provide the ability to use TECs to chill wells to 4° after PCR is complete. Such cooling ability allows sample recovery after completion of PCR. In yet another advantageous aspect, the disclosed configuration provides individual well calibration to overcome manufacturing variability or defects. For example, a particular well may need more power to operate due to manufacture and packaging process. Calibration of this particular well is made possible by the thermal ground.

Traditional PCR instruments are large, power hungry, heavy, and typically coupled to additional interfaces with electronics to pass or store data. These instruments are also very expensive. For example, a traditional large bench-top thermal cycling instrument typically costs between $40,000 and $100,000. This patent document further describes an integration of solid-state thermocycling technology to transform benchtop instruments into portable systems that includes integration, packaging, and fusion of the solid-state thermocycler onto a compatible interface for power, control, and communication.

Figure 6:
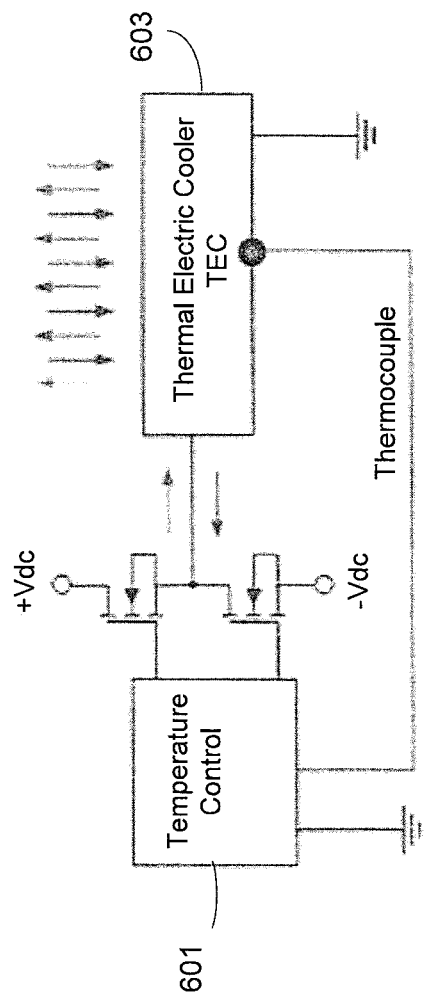
FIG. 6 shows a schematic diagram for exemplary controls by the TEC in their simplest form.

FIG. 6 shows a schematic diagram for exemplary controls by the TEC in their simplest form. The controls in this particular embodiment include a temperature control 601 that is thermocoupled to a TEC component 603. An array of miniaturized TEC components 603 can be integrated into a portable electronic interface, such as a USB interface, to form a portable lab system. The USB interface can provide the necessary power, ground connection, and dedicated data lines for the miniaturized TEC components 603. FIG. 7 illustrates exemplary pin assignments for a USB 3.1 standard-A connector, wherein VBUS pin provides the power, GND pin provides the ground for power return, and D− and D+ are the differential pair as dedicated data lines. For example, a high-power SuperSpeed interface can provide voltage at 5V and up to 900 mA. A Type-C interface can provide voltage up to 20V at 5 A. Furthermore, power can be doubled by a Y-connector tapping into an additional open USB port on the PC or electronic device.

Such portable lab systems can reduce the cost of thermal cycling instruments. In some embodiments, the system can include a single well to test one sample at a time. The system can also include multiple independent wells to conduct test for different samples at the same time.

In some embodiments, when power is limited, the system slows the rate of TEC pumping accordingly. The system can also charge a battery or capacitor when it is plugged into a host computing device, and, when external power from the host computing device is unavailable, provide additional power on demand as thermocycling needs.

Figure 8:
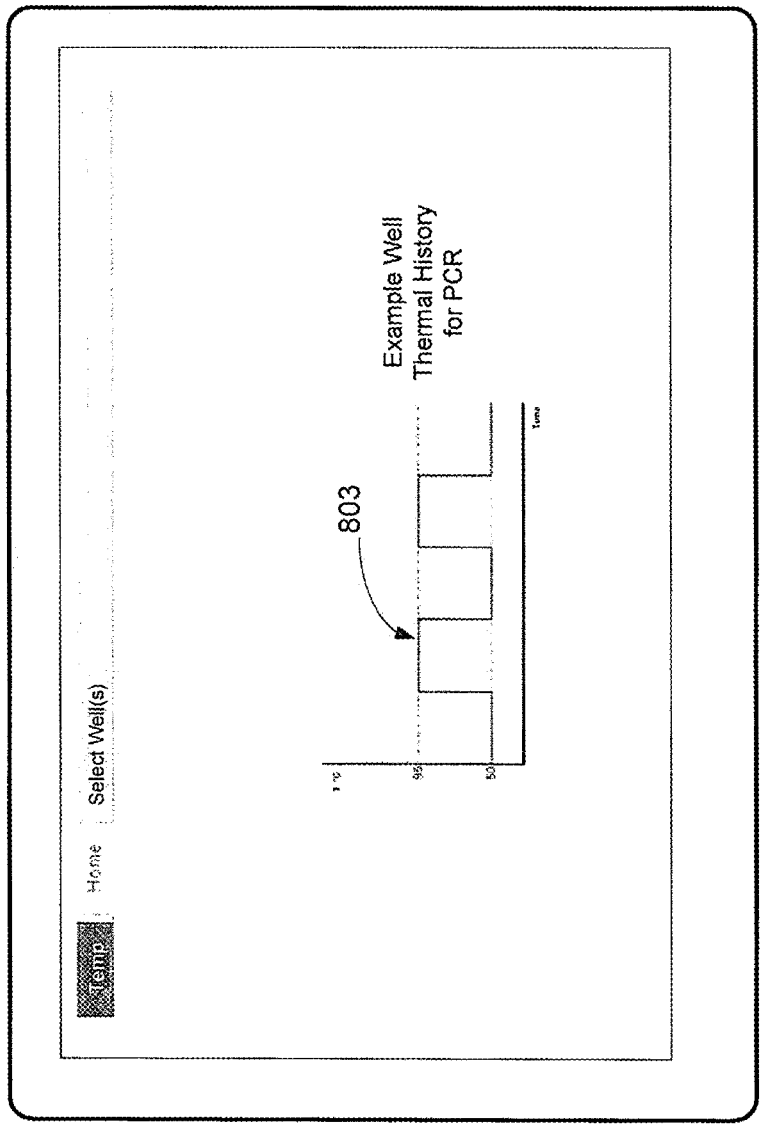
FIG. 8 shows an exemplary user interface indicating the current temperature of the wells.

In some embodiments, the system includes a control software installed on the portable electronic interface. When the system is plugged into the host computing device, e.g. a personal computer (PC) or a mobile device, the software can open a user interface window on the host computing device to indicate the state of operation of the thermal cycler. The user interface window can be a pop-up window on PC or an interface of mobile application on a mobile device or other portable devices. As illustrated in FIG. 8, the user interface 801 can demonstrate current thermocycling temperatures 803 of all wells or a set of selected wells. It can also display other operating parameters, such as PCR signal amplitudes. The control software is capable of compiling test data and transmit the data over the network, via the host computing device, to hospitals or physicians' offices. The inclusion of the control software on the electronic interface increases portability in the thumb-drive sized package for the thermocycler, and allows PCR testing to be conducted in neighborhood pharmacies instead of dedicated labs.

In some embodiments, to maintain the device at a comfortable touching temperature, a simple fan can be used. For example, a commercially available miniature fan that moves 1.5 L of air per minute at 3 volts DC can be integrated as a part of the system. The fan can be positioned inside the casing of the system so that the casing can protect it from external damage.

The system can be reusable to reduce the cost of PCR testing. However, in some embodiments, dongles of the testing system can be disposable for biohazardous applications or when re-use is not desired. Alternatively, the dongles can be fitted with disposable sample inserts that contain the sample and seal it, maintaining thermal contact with the wells.

While the embodiments of the system described herein fit onto a USB dongle that is approximately the size of a human thumb, other geometries and interfaces are also possible for the integration. Other electronic interfaces that include a power supply and communication capabilities can be used to integrate the array of miniaturized TEC components. In some embodiments, a FireWire interface can be used.

This integrated configuration of the extremely efficient solid-state thermal cycler can enable an estimated thermal cycling time of 5 seconds for the temperature to go from 50° to 95° for one to four wells under a current between 0.25 to 0.5 A. The sizes of the wells can be 1.25, 2.5, 5, and 10 µL in volume. A plurality of wells can be selected with an appropriate volume for the available power and desired cycle times. Similarly, cycle time from 95° to 50° is estimated to be around 5 seconds. A system having multiple wells of 0.5 to 20 µL in volume can perform complete cycles on the order of 8 to 40 seconds depending on desired number of wells, volume, available power and current.

Figure 9:
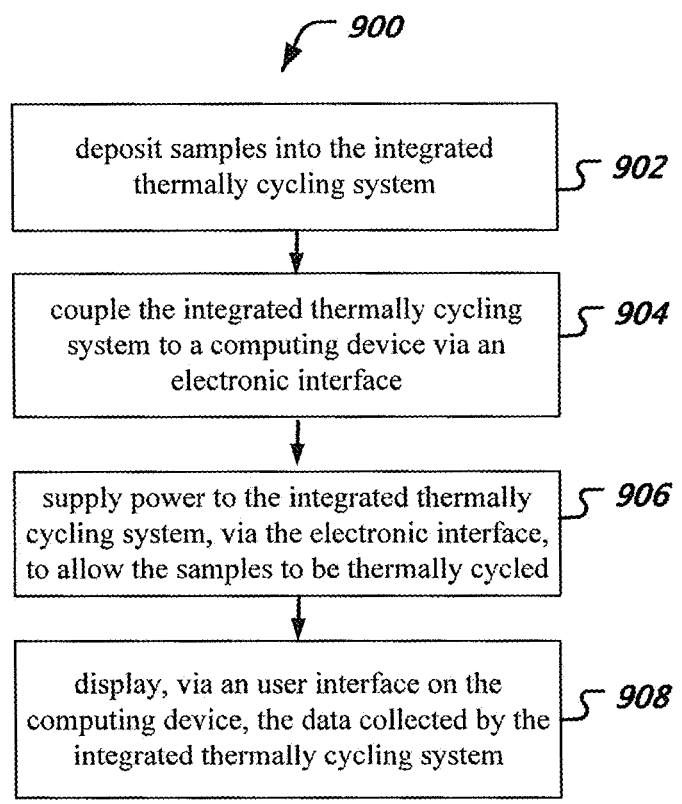
FIG. 9 shows an exemplary flow chart for a method of operating an integrated thermal cycling system.

FIG. 9 shows an exemplary flowchart for a method 900 of operating an integrated thermal cycling system. The method can be implemented on the portable lab system described above. The method 900 includes: at 902, depositing samples into the integrated thermal cycling system; at 904, coupling the integrated thermal cycling system to a computing device via an electronic interface; at 906, supplying power to the integrated thermal cycling system, via the electronic interface, to allow the samples to be thermally cycled; and, at 908, displaying, via a user interface on the computing device, the data collected by the integrated thermal cycling system.

This patent document provides a method to integrate aspects of a large bench-top thermal cycling instrument onto a USB dongle or other similar PC or mobile electronics interface. The integrated system employs efficient solid-state thermal cycling, processing, microcontroller operation, and power and data interfacing such that the entire instrument is miniaturized and packaged into a thumb-drive sized system. The integrated system eliminates the external instrument and replaces it with a functional USB-sized device. This integrated system can be placed in an optical scanner, for example, to have the sealed wells "read" for chemical reaction products using optical probes for fluorescence or chemiluminescence. Non-optical methods for detection and reaction monitoring may also be employed, such as electrochemical detection. The integration of the thermocycler onto a programmable device provides portable power, immediate and simple software interface, and communication with embedded PC or mobile applications.

Some of the embodiments described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media can include a non-transitory storage media. Generally, program modules may include routines, programs, objects, components, data structures, etc. that perform particular tasks or implement particular abstract data types. Computer- or processor-executable instructions, associated data structures, and program modules represent examples of program code for executing steps of the methods disclosed herein. The particular sequence of such executable instructions or associated data structures represents examples of corresponding acts for implementing the functions described in such steps or processes.

Some of the disclosed embodiments can be implemented as devices or modules using hardware circuits, software, or combinations thereof. For example, a hardware circuit implementation can include discrete analog and/or digital components that are, for example, integrated as part of a printed circuit board. Alternatively, or additionally, the disclosed components or modules can be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities of this application. Similarly, the various components or sub-components within each module may be implemented in software, hardware or firmware. The connectivity between the modules and/or components within the modules may be provided using any one of the connectivity methods and media that is known in the art, including, but not limited to, communications over the Internet, wired, or wireless networks using the appropriate protocols.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

In this document, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

Only a few implementations and examples are described and other implementations, enhancements and variations can be made based on what is described and illustrated in this patent document.

What is claimed is:

1. A method of operating an integrated thermal cycling system, comprising:

depositing samples into the integrated thermal cycling system, wherein the integrated thermal cycling system comprises a thermal cycling device and an electronic interface, wherein the thermal cycling device comprises: multiple wells to receive the samples to be thermally cycled, a thermoelectric cooling (TEC) element connected to the multiple wells, a substrate on which the TEC element is positioned, and a controller coupled to the TEC element to control operation of the TEC element, wherein the multiple wells are positioned within the substrate, and wherein the substrate comprises a thermally conductive ground positioned between adjacent wells;

coupling the integrated thermal cycling system to a computing device via the electronic interface;

supplying power to the integrated thermal cycling system, via the electronic interface, to allow the multiple wells to exchange heat with the substrate and to allow each well of the multiple wells to operate independently from one another;

wherein supplying of the power to the integrated circuit comprises: transferring energy from a first well to a second well of the multiple wells when current flows through the TEC element in a first direction, and from the second well to the first well of the multiple wells when current flows through the TEC element in a second direction; and collecting data from the controller of the integrated thermal cycling system via a data line.

2. The method of claim 1, comprising: connecting the computing device to a network, and transmitting, via a network interface on the computing device, the data collected by the integrated thermal cycling system to other computing devices on the network.

3. The method of claim 1, comprising: displaying, via a user interface on the computing device, the data collected by the integrated thermal cycling system.

4. The method of claim 1, wherein the samples in at least one well of the multiple wells have a different thermal set point and a different cycle duration compared to samples in at least another one of the multiple wells.

5. The method of claim 1, wherein the electronic interface is one of a USB interface or a FireWire interface.

6. The method of claim 1, wherein the computing device is one of a personal computer or a mobile device.

7. The method of claim 1, wherein the thermally conductive ground is a thermal ground lattice, line, trace, or plane.

8. The method of claim 1, wherein the thermally conductive ground has a grid geometry between the adjacent wells.

9. The method of claim 1, wherein the thermally conductive ground has a rectilinear shape outside of the multiple wells.

10. The method of claim 1, wherein the thermally conductive ground forms a concentric ring outside or inside of the multiple wells.

11. The method of claim 1, further comprising: operating the integrated thermal cycling system at a cycle time of approximately 5 seconds and a temperature from 95° to 50° Celsius.

12. The method of claim 1, wherein each well of the multiple wells is insulated from any other well of the multiple wells, and each well of the multiple wells is in thermal contact with at least a portion of the TEC element and with the thermally conductive ground.

13. The method of claim 1, further comprising providing a fan to maintain a temperature of the integrated thermal cycling system at a range of temperatures.

14. The method of claim 1, wherein depositing the samples into the integrated thermal cycling system includes depositing a first set of samples into a first well of the multiple wells and a second set of samples into a second well of the multiple wells, and wherein the method comprises operating the first well of the multiple wells based on a first thermocycling temperature, and operating the second well of the multiple wells independently from the first well of the multiple wells based on a second thermocycling temperature.

15. The method of claim 14, wherein operating the first and the second wells of the multiple wells are carried out concurrently.

16. The method of claim 1, further comprising calibrating at least one of the multiple wells independently from at least another one of the multiple wells.

\* \* \* \* \*